(12) United States Patent
Kang

(10) Patent No.: US 12,138,014 B2
(45) Date of Patent: Nov. 12, 2024

(54) APERTURELESS CONFOCAL MICROSCOPY DEVICES AND METHODS

(71) Applicant: Arizona Board of Regents on Behalf of the University of Arizona, Tucson, AZ (US)

(72) Inventor: Dongkyun Kang, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 929 days.

(21) Appl. No.: 17/266,888

(22) PCT Filed: Aug. 7, 2019

(86) PCT No.: PCT/US2019/045463
§ 371 (c)(1),
(2) Date: Feb. 8, 2021

(87) PCT Pub. No.: WO2020/033518
PCT Pub. Date: Feb. 13, 2020

(65) Prior Publication Data
US 2021/0307612 A1 Oct. 7, 2021

Related U.S. Application Data

(60) Provisional application No. 62/715,953, filed on Aug. 8, 2018.

(51) Int. Cl.
*A61B 5/00* (2006.01)
*G01J 3/02* (2006.01)
(Continued)

(52) U.S. Cl.
CPC .......... *A61B 5/0068* (2013.01); *G01J 3/0208* (2013.01); *G01J 3/2823* (2013.01);
(Continued)

(58) Field of Classification Search
CPC .... A61B 5/0068; G01J 3/0208; G01J 3/0229; G01J 3/2833; G02B 21/0032; G02B 21/006; G02B 21/0064; G02B 21/361
See application file for complete search history.

(56) References Cited

U.S. PATENT DOCUMENTS

| 8,773,757 B2 | 7/2014 | Chen et al. |
| 9,625,628 B2 | 4/2017 | Hruska et al. |

(Continued)

FOREIGN PATENT DOCUMENTS

WO 2015105870 A1 7/2015

OTHER PUBLICATIONS

International Search Report and Written Opinion mailed Oct. 29, 2019 for International Patent Application No. PCT/US2019/045463 (10 pages).

*Primary Examiner* — Chao Sheng
(74) *Attorney, Agent, or Firm* — Perkins Coie LLP

(57) ABSTRACT

Methods, devices and systems for confocal microscopy of human tissues or other samples are described that can be manufactured at a low cost, and are small and portable. One apertureless confocal microscope includes a dispersion element that produces output beams having different spectral components for illumination of a target, such as a tissue. The confocal microscope also includes one or more lenses that receive reflected beams from the target and focus the reflected beams onto a linear variable filter. The linear variable filter is positioned to receive the focused light to allow a particular range of spectral components of light to pass through the linear variable filter that is a function of a spatial location of the focused light incident on the linear variable filter. The described confocal microscopes, among other features and benefits, can greatly facilitate disease diagnosis in medical applications.

21 Claims, 11 Drawing Sheets

(51) Int. Cl.
*G01J 3/28* (2006.01)
*G02B 21/00* (2006.01)
*G02B 21/36* (2006.01)

(52) U.S. Cl.
CPC ....... *G02B 21/0032* (2013.01); *G02B 21/006* (2013.01); *G02B 21/0064* (2013.01); *G02B 21/361* (2013.01); *G01J 2003/2826* (2013.01)

(56) References Cited

U.S. PATENT DOCUMENTS

| | | |
|---|---|---|
| 2008/0064925 A1 | 3/2008 | Gill et al. |
| 2010/0188742 A1* | 7/2010 | Chen ................ G02B 21/0064 359/615 |
| 2015/0219494 A1* | 8/2015 | Hruska ................ G01J 3/2803 356/326 |
| 2017/0124370 A1 | 5/2017 | He et al. |
| 2018/0017772 A1 | 1/2018 | Arbore et al. |

* cited by examiner

APERTURELESS CONFOCAL MICROSCOPY DEVICES AND METHODS

CROSS REFERENCE TO RELATED APPLICATIONS

This patent document is a 371 National Phase Application of International Patent Application No. PCT/US2019/045463, filed Aug. 7, 2019, which claims priority to the provisional application with Ser. No. 62/715,953, titled "Apertureless Confocal Microscopy Devices and Methods," filed Aug. 8, 2018. The entire contents of the above noted applications are incorporated by reference as part of the disclosure of this document.

TECHNICAL FIELD

The subject matter of this patent document generally relates to confocal microscopes, and more particularly to apertureless confocal microscopy systems, devices and methods.

BACKGROUND

Since their invention in the 1950s, confocal microscopes have been extensively investigated to provide better imaging performance for applications that range from metrology to tissue imaging. In its basic configuration, a confocal microscope is a point imaging system that includes a pinhole to block out the light outside of the focused spot before reaching a detector. Over the years, many variations and improvements to the original confocal microscope have been proposed and implemented. Despite such improvements, the existing confocal microscopes still fail to satisfy the needs for a low-cost system that excludes moving parts, while at the same time has a compact and simple form factor.

SUMMARY OF CERTAIN EMBODIMENTS

The disclosed technology relates to methods, devices and systems for confocal microscopy of human tissues or other samples that, among other features and benefits, can be manufactured at a low cost, and are small and portable. The confocal microscopes developed based on the disclosed technology, while applicable to other areas of technology, can greatly improve clinical utility of the confocal microscopy technology and facilitate disease diagnosis in medical applications.

One aspect of the disclosed embodiments relates to an apertureless confocal microscope that includes an optical element positioned to receive a light beam and to produce output beams having different spectral components for illumination of a target. The apertureless confocal microscope further includes one or more lenses positioned to receive reflected beams from the target upon reflection of the output beams from the target, and to focus the reflected beams onto a linear variable filter. The linear variable filter is positioned to receive the focused light from the one or more lenses and to allow a particular range of spectral components of light incident thereon to pass therethrough as a function of a spatial location of the focused light incident on the linear variable filter.

Another aspect of the disclosed embodiments relates to an apertureless confocal microscope that includes a high dispersion lens positioned to receive a line output beam from a light source and to illuminate a target such that light having different spectral contents are focused onto different depths of the target. The confocal microscope further includes at least another lens positioned to receive reflected light from the target, and to focus the reflected light onto a linear variable filter. The linear variable filter is positioned to receive the focused light from the at least another lens and to allow a particular range of spectral components of light incident thereon to pass therethrough as a function of a spatial location of the focused light incident on the linear variable filter.

DETAILED DESCRIPTION

In the present document, the word "exemplary." is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

Figure 1B:
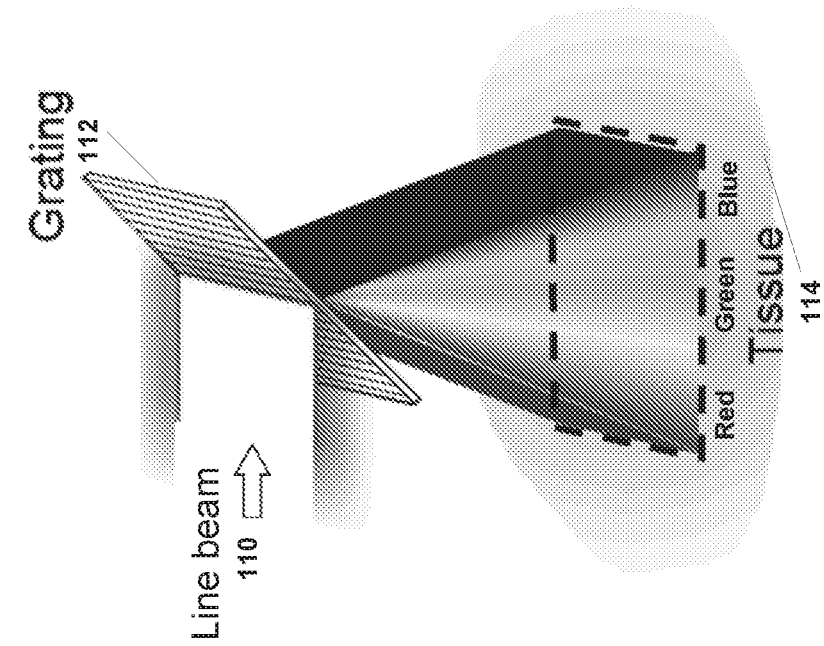
FIG. 1B illustrates an example another conventional confocal microscope that uses a diffraction grating to effectuate beam scanning.
Figure 1A:
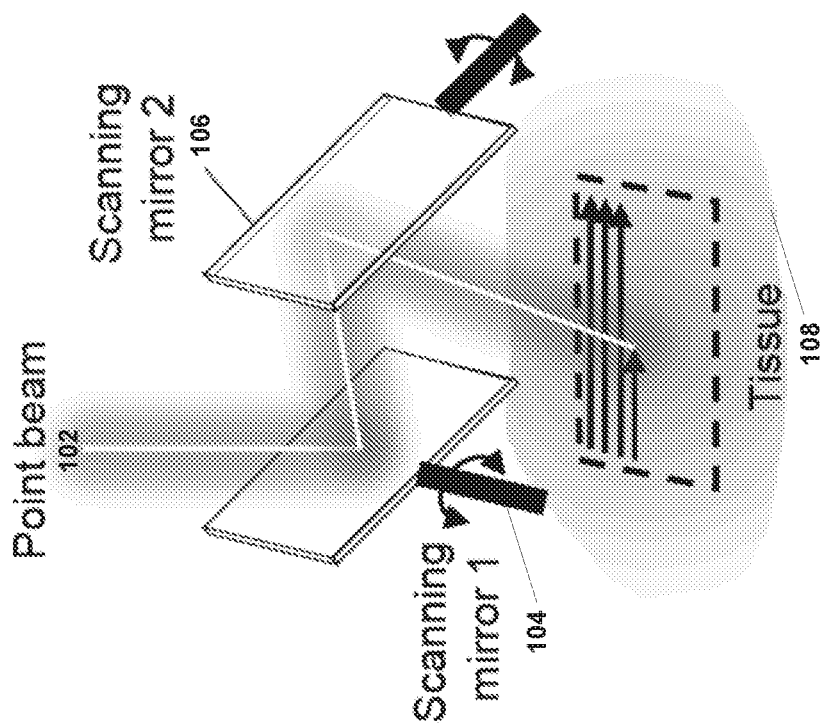
FIG. 1A illustrates an example conventional confocal microscope.

As noted earlier, conventional confocal microscopes suffer from several shortcomings. FIG. 1A is provided to illustrate the principles of operations of a conventional confocal microscope. In FIG. 1A, the tissue 108 or object of interest is scanned by a point beam 102 using scanning mirror 1 (104) and scanning mirror 2 (106), or generally via beam scanning devices such as galvo scanners and polygon mirrors, to obtain two-dimensional confocal images. An improvement over the configuration of FIG. 1A is shown as a scan-less confocal microscope in FIG. 1B, in which a diffraction grating 112 receives a line beam 110 and produces diffracted output light (e.g., spanning red to green to blue components) to effectuate spatial scanning of the object 114 and to obtain two dimensional confocal images without having to use any beam scanning devices.

Figure 2:
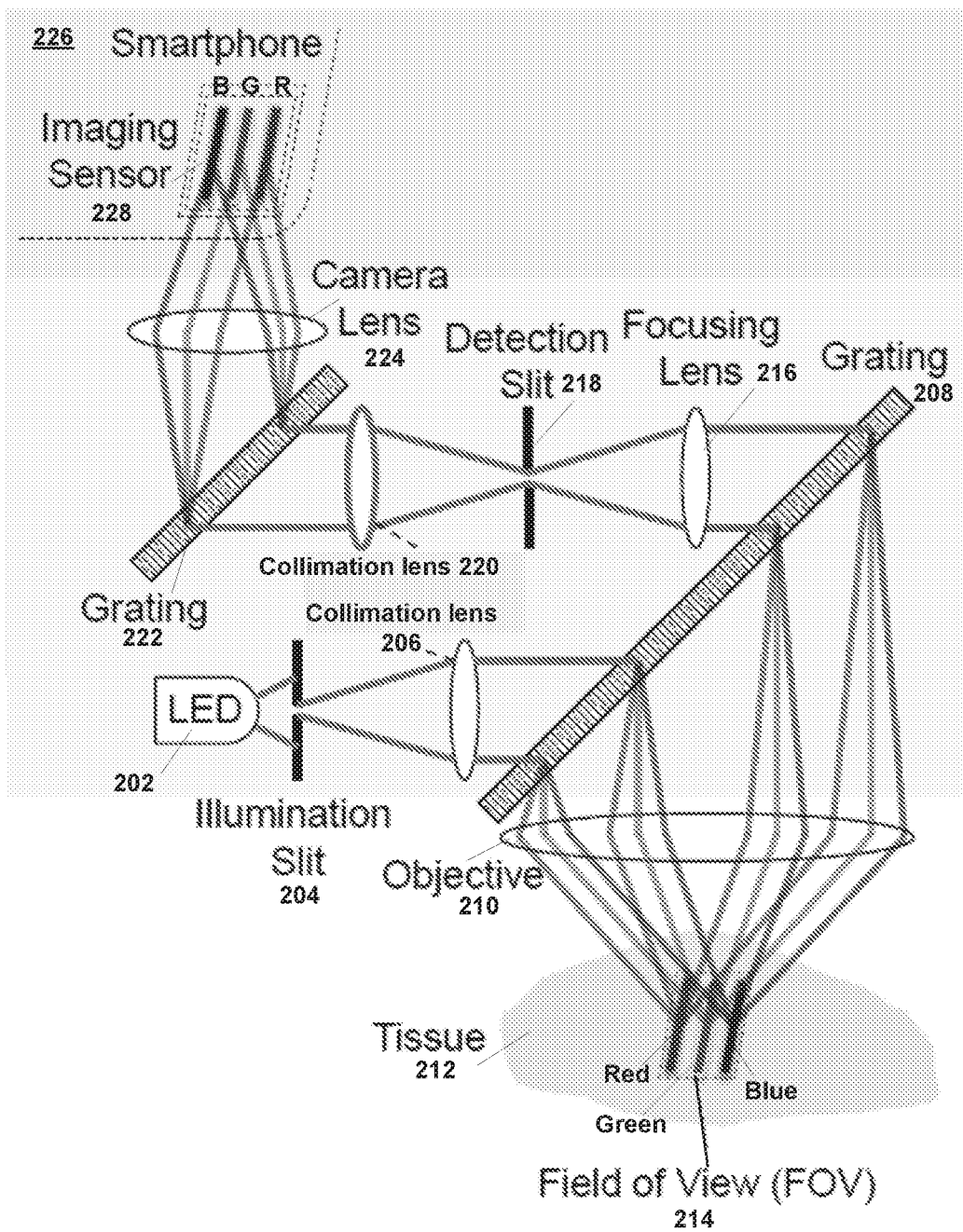
FIG. 2 illustrates a scan-less confocal microscope constructed for use with a smartphone.

The scan-less confocal microscope can be further configured to construct a smartphone-based confocal microscope, as shown in FIG. 2. In this approach, a light source 202 (e.g., an LED) is used along with an illumination slit 204 and a collimating lens 206 to illuminate a grating 208 that effectuates the scanning. In FIG. 2, the field of view (FOV) 214 of the system is illustrated by the rectangular dashed box over the tissue 212. The reflected light from the tissue is collected by the objective lens 210, diffracted by the grating 208, provided to a focusing lens 216 that provides the focused light to a slit 218 to filter the light and to achieve confocal optical sectioning. Light filtered by the slit 218 is expanded using another collimation lens 220 and another grating 224, is passed through a camera lens 224 to generate a two-dimensional confocal image, which is acquired by an imaging sensor 228 of a smartphone 226. The imaging sensor 228 can be an imaging sensor inside a smartphone camera. This approach does not require the use of expensive beam scanners, associated controllers, high-bandwidth detectors and digitizers, and therefore can reduce the device cost (e.g., from over $65,000 to about $4,000). However, the configuration of FIG. 2 still includes a detection slit 218 aperture, two gratings 208, 222, and two lenses 216, 224. Elimination of at least some of these components can reduce the complexity and the cost of the system to facilitate assembly, distribution and implementation of the devices. For example, the system of FIG. 2 still requires precision alignment of the detection slit 218 aperture, which requires the use of precision translation stages and high-quality lenses around it, thus hampering further reduction of the device cost and size.

The disclosed embodiments relate to confocal microscopy devices and associated methods that enable implementation of cost-effective, simple and small devices that can conduct confocal microscopy without using any detection apertures. The disclosed devices and methods for confocal microscopy eliminate or reduce the complexity of alignment and assembly issues, and allow a reduction in both the cost and the size of confocal microscopes, thus facilitating the use and proliferation of confocal microscopes in existing and new applications. The disclosed "apertureless" devices and methods can, for example, be used for skin disease diagnosis, and can be implemented as a low-cost confocal endoscope for gastrointestinal applications. Another application of the disclosed technology includes implementation for a trans-display fingerprint recognition module in a smartphone. Additional non-exhaustive example applications of the disclosed technology include implementations for specimen inspection, semiconductor inspection and imaging, educational uses in classrooms, and others.

It should be noted that the term "apertureless" in the present document is used to convey the lack of a detection aperture that is typically positioned at the detection focal point in the context of a confocal microscope. Furthermore, the disclosed embodiments are sometimes described using a "tissue" as an example of part of a target that is imaged or examined by a confocal microscope. It is, however, understood that other objects or targets can be imaged or viewed by the disclosed devices.

Figure 3:
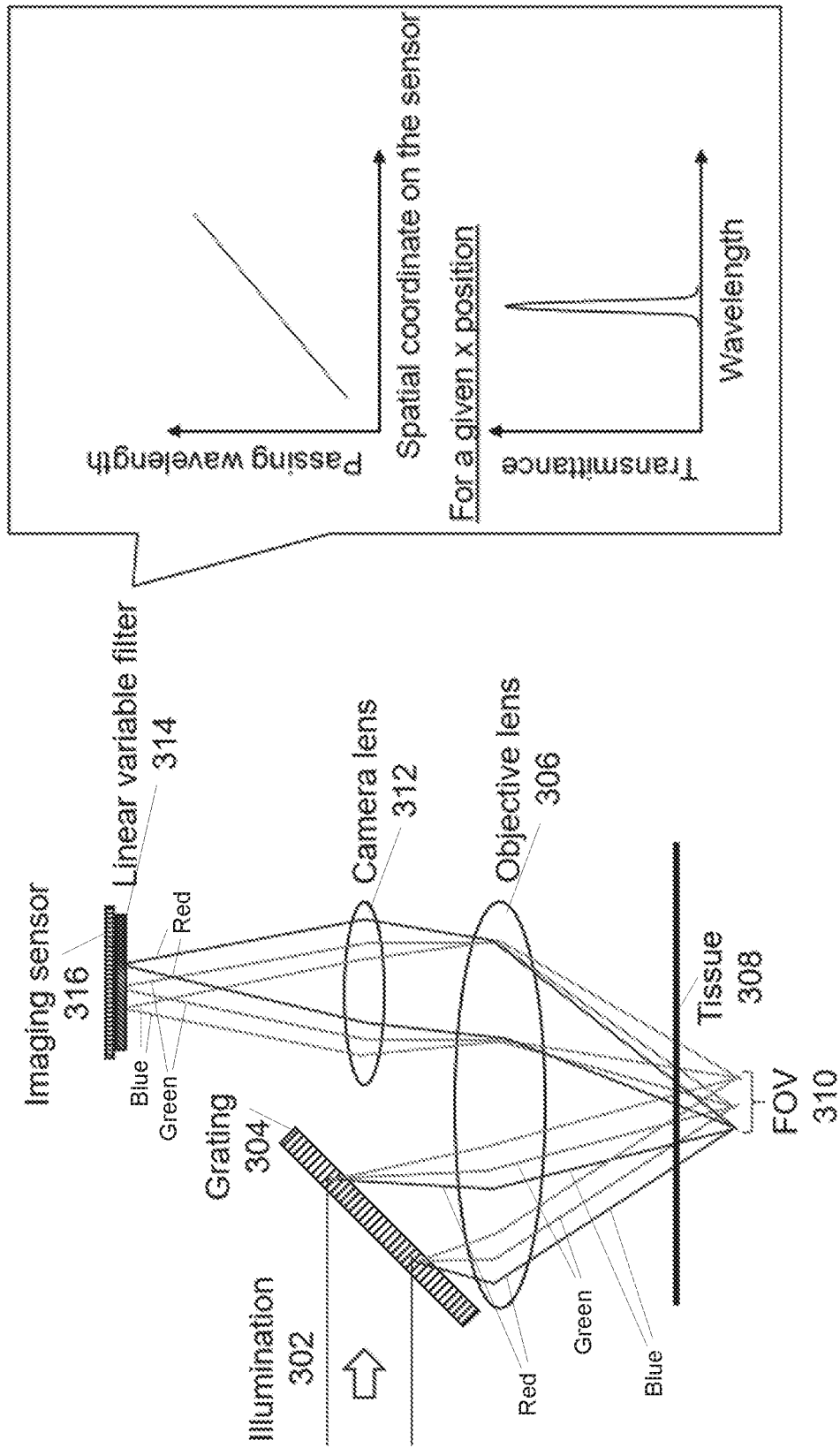
FIG. 3 illustrates an apertureless confocal microscope in accordance with an exemplary embodiment.

FIG. 3 illustrates an apertureless confocal microscope in accordance with an exemplary embodiment. The configuration in FIG. 3 does not include a detection slit aperture that is a hallmark of typical confocal microscopes for optical sectioning. As shown in FIG. 3, illumination 302 is provided to the grating 304 that illuminates the tissue 308 through the objective lens 306: the light returning from the tissue 308 is focused on a linear variable filter 314 via an imaging lens 312, which generates a two-dimensional image on the imaging sensor 316. Example characteristics of the linear variable filter are shown on the right-hand side of FIG. 3, indicating a linear relationship between the spatial coordinate on the linear variable filter 314 (and thus the sensor 316) and the wavelength that passes through the linear variable filter 314. As shown in the lower plot, for each pixel on the imaging sensor 316, only a narrow spectrum of light is allowed to pass through the linear variable filter 314. Therefore, each pixel of the sensor 316 works as a confocal detection aperture. By not having to use a detection slit aperture, this configuration obviates the need for several optical elements, including two gratings, two lenses, and detection slit, and therefore reduces the device cost and size.

In one example design, with a groove density of grating (g), central wavelength of the illumination source ($\lambda_c$) and a bandwidth ($\Delta\lambda$), objective focal length ($f_{OL}$), the field of view (FOV) on the tissue is determined as:

$$FOV = \frac{g\Delta\lambda f_{OL}}{\cos\theta_i}, \qquad \text{Eq. (1)}$$

where $\theta_i$ is the incidence angle on the grating and often set as the Bragg angle for the central wavelength for the given groove density. For an example groove density of 1379 lines-per-mm, central wavelength of 595 nm, bandwidth of 80 nm, objective lens focal length of 5 mm, the incidence angle is set at 24.2° and the corresponding FOV is 605 µm.

In the example configuration of FIG. 3, reflected light from the tissue 310 is focused as an image on the linear variable filter 314. The extent of the image on the linear variable filter 314 is determined by the magnification between the objective lens 306 and camera lens 312 and the FOV 310. For an exemplary linear variable filter with the central pass wavelength variation rate of 14.3 nm/mm (i.e., the central pass wavelength changes from 450 nm to 950 nm over a 35 mm length of the linear variable filter), the 80-nm source bandwidth corresponds to 5.6 mm length for the filter. Therefore, the magnification between the objective lens 306 and camera lens 312 can be set as 5.6/0.605=9.26 to ensure that each wavelength of the reflected light focused on the linear variable filter 314 is closely matched to the central pass wavelength of the filter at the focused spot. The camera lens focal length can be set to 46.3 mm to achieve the magnification of 9.26.

Figure 4:
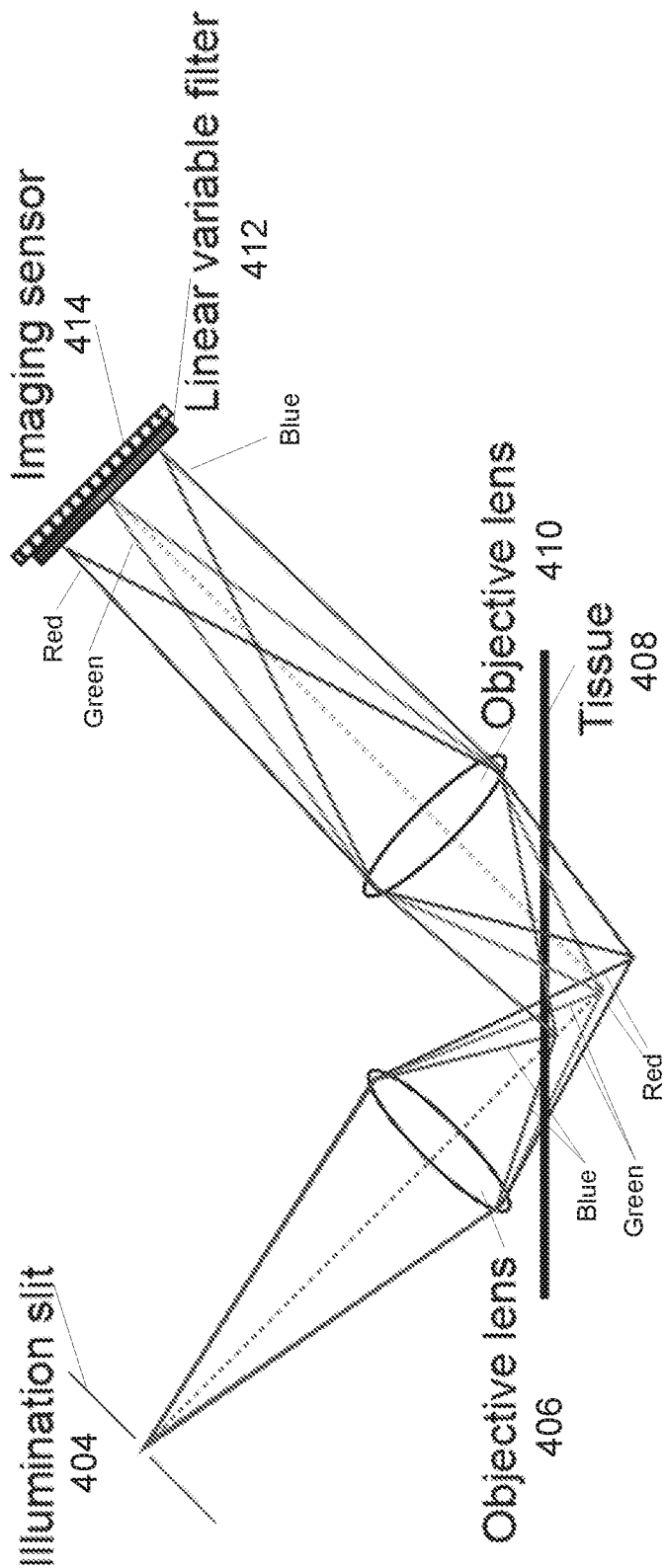
FIG. 4 illustrates another apertureless confocal microscope configured for oblique tissue imaging in accordance with an exemplary embodiment.

In the configuration of FIG. 3, the optical axis of the lenses is substantially perpendicular to a surface of the target. In some embodiments, the apertureless confocal microscope can also be configured for oblique tissue imaging as shown in the exemplary embodiment of FIG. 4. In this configuration, light from an illumination slit 404 or a linear source is focused on multiple lines through an objective lens 406 with high dispersion (e.g., a hyperchromatic objective lens). The dispersion of the objective encodes each imaging depth with a unique wavelength, resulting in two-dimensional oblique illumination. Light reflected from the tissue 408 is focused on the linear variable filter 412 by another objective lens 410 without high dispersion, and is detected by the imaging sensor 414. The variable linear filter 412 enables confocal optical sectioning as discussed earlier. In the configuration of FIG. 4, images are associated with different depths within the tissue, and additional scanning mechanisms (with or without any moving components) may be added to enable full spatial scans across the tissue sample. The configuration of FIG. 4 can be designed to have different fields of view and magnification characteristics. In some example designs, an FOV in the range 1-2 mm can be achieved.

Figure 5:
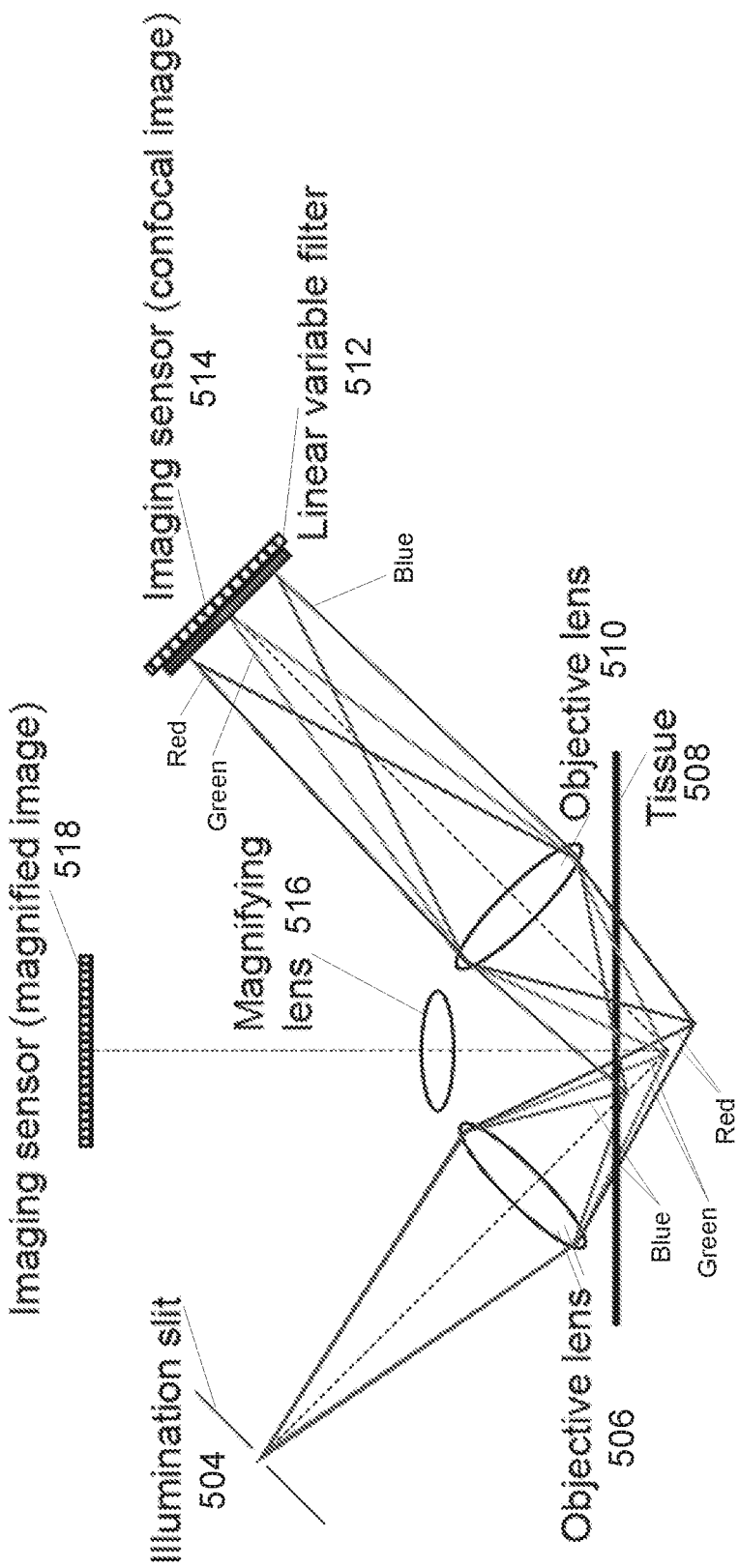
FIG. 5 illustrates another apertureless confocal microscope configured for oblique tissue imaging, which includes magnification optics and additional imaging sensor in accordance with an exemplary embodiment.

In some applications, such as for dermatologic applications, additional magnifying optics can be used to provide wide-field images of, for example, the skin lesion. The oblique confocal microscope configuration that is, for example, illustrated in FIG. 4, leaves room at the center of the field of view to include magnifying optics and an imaging sensor associated with it. One such exemplary embodiment is illustrated in FIG. 5, which includes an illumination slit 504, a first objective lens 506 that is used for illumination the tissue 508, a second objective lens 510, a linear variable filter 512 and a first imaging sensor 514 similar to those described in FIG. 4, in addition to a magnifying lens 516 and an imaging sensor 518 that produce a magnified view of the tissue 508 under examination.

Figure 6:
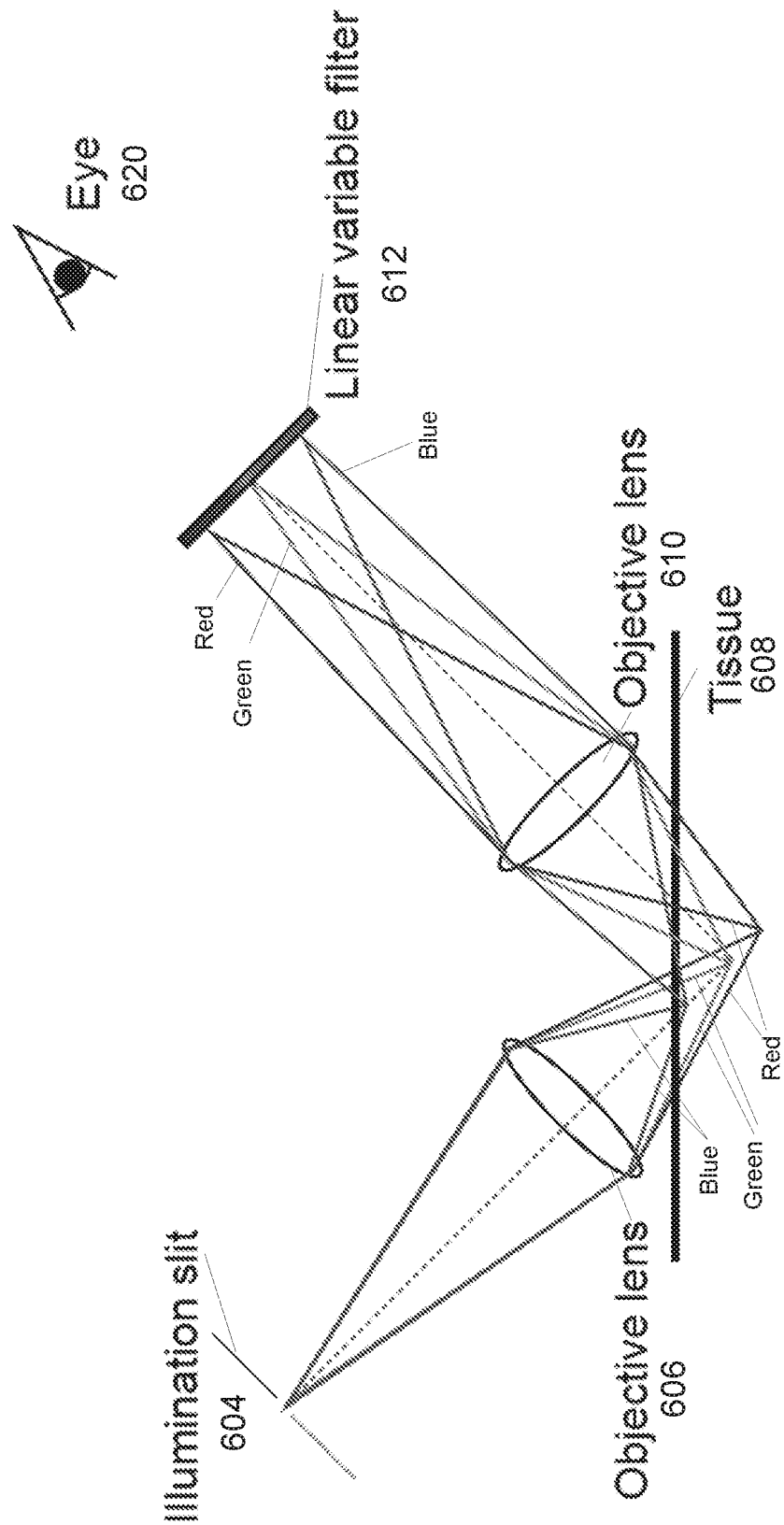
FIG. 6 illustrates another apertureless confocal microscope configured for oblique tissue imaging and adapted for viewing with human eyes in accordance with an exemplary embodiment.

In some embodiments, the apertureless confocal microscope can be further configured without an imaging sensor to allow for direct view with human eyes. One such example configuration is illustrated in FIG. 6, which includes similar components as those in FIG. 4 (an illumination slit 604, a first objective lens 606 that directs the illumination to the tissue 608, as second objective lens 610 and a linear variable filter 612) but excludes the imaging sensor. In this embodiment, a human eye 620 is used to perceive the confocal images generated on the linear variable filter 612.

Figure 7:
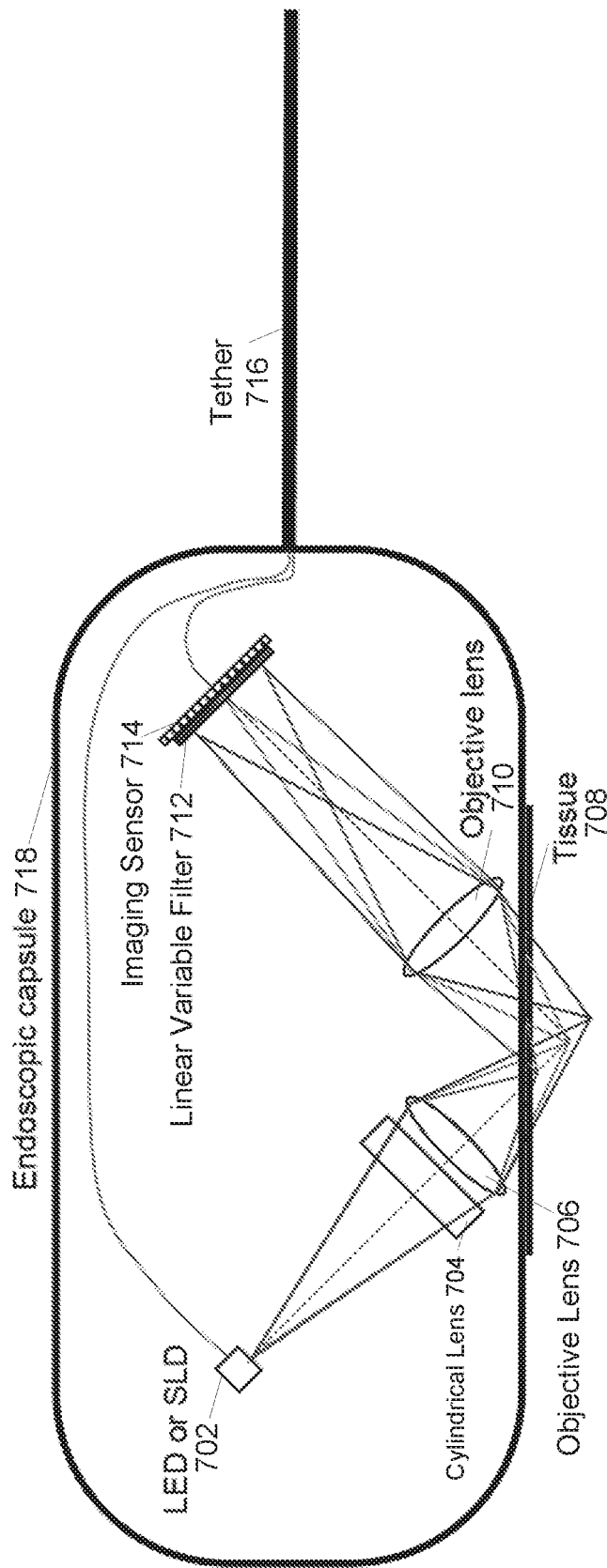
FIG. 7 illustrates an implementation of a confocal microscopy system in a tethered endoscope in accordance with an exemplary embodiment.

The small size and simple structure of the disclosed apertureless confocal microscopes can also enable low-cost, and compact devices for imaging inside narrow passageways and hard-to-reach places, with applications in endomicroscopy, robotic surgery, and the like. One example embodiment, illustrating a tethered endoscope is shown in FIG. 7. In the configuration of FIG. 7, a broad spectra light source 702, such as a LED or super luminescent diode (SLD) is used as a point source, and light from the point source is focused by a cylindrical lens 704 and a first objective lens 706 to generate spectrally-encoded oblique illumination into the tissue 708. The light reflected from the tissue 708 is focused by the second objective lens 710 onto the linear variable filter 712 that allows spectrally filtered light to reach the imaging sensor 714, as described in connection with previous configurations. A miniature camera can be used to implement the imaging sensor 714 (e.g., a CCD sensor). The configuration of FIG. 7 includes an endoscopic enclosure 718 that can be shaped as a capsule having at least one transparent section (or window) that allows the light to be directed to, and received from, the tissue 708. In an example implementation, the endoscope enclosure 718 can be made smaller than 12.7 mm in diameter (e.g., as small as 7 mm) for easy introduction to esophagus, stomach, and duodenum. The confocal endoscopic capsule can be used to, for example, examine cellular changes associated with gastroesophageal diseases such as Barrett's esophagus and eosinophilic esophagitis.

In some embodiments, the cylindrical lens 704 and the first objective lens 706 can be replaced with a line source and a high dispersion element, similar to the configuration that is shown in FIG. 4. The example configuration of FIG. 7 includes a tether 716 that can be used for navigation, insertion and removal of the endoscope, as well as for allowing power and/or other electrical signals to be communicated to/from the components inside the capsule 718.

In some exemplary embodiments, the tether 716 is removed and all communications to/from the confocal microscope can be effectuated via wireless means. For example, the capsule 718 can include an antenna and a capacitor that is charged when the antenna is exposed to an RF field of a particular frequency. The capsule 718 can also include a processor, a memory and associated circuitry to provide signal processing and storage capabilities within the capsule 718, and to allow one or more wireless communication protocols to be implemented. In some embodiments, the endoscopic system can include a battery as a power source.

In some embodiments, more than one confocal microscope can be implemented within a single endoscopic capsule or enclosure. In such embodiments, similar confocal microscope configurations (or at least portions thereof) can be duplicated and positioned at different locations within the capsule to allow acquisition of different images (e.g., images from different angles, images from different spatial locations, images produced based on different FOVs, etc.). The obtained images can be processed separately or collectively to, for example, enable the production of enhanced images with better image quality, larger FOV, 3-dimensional images, and the like.

Figure 8:
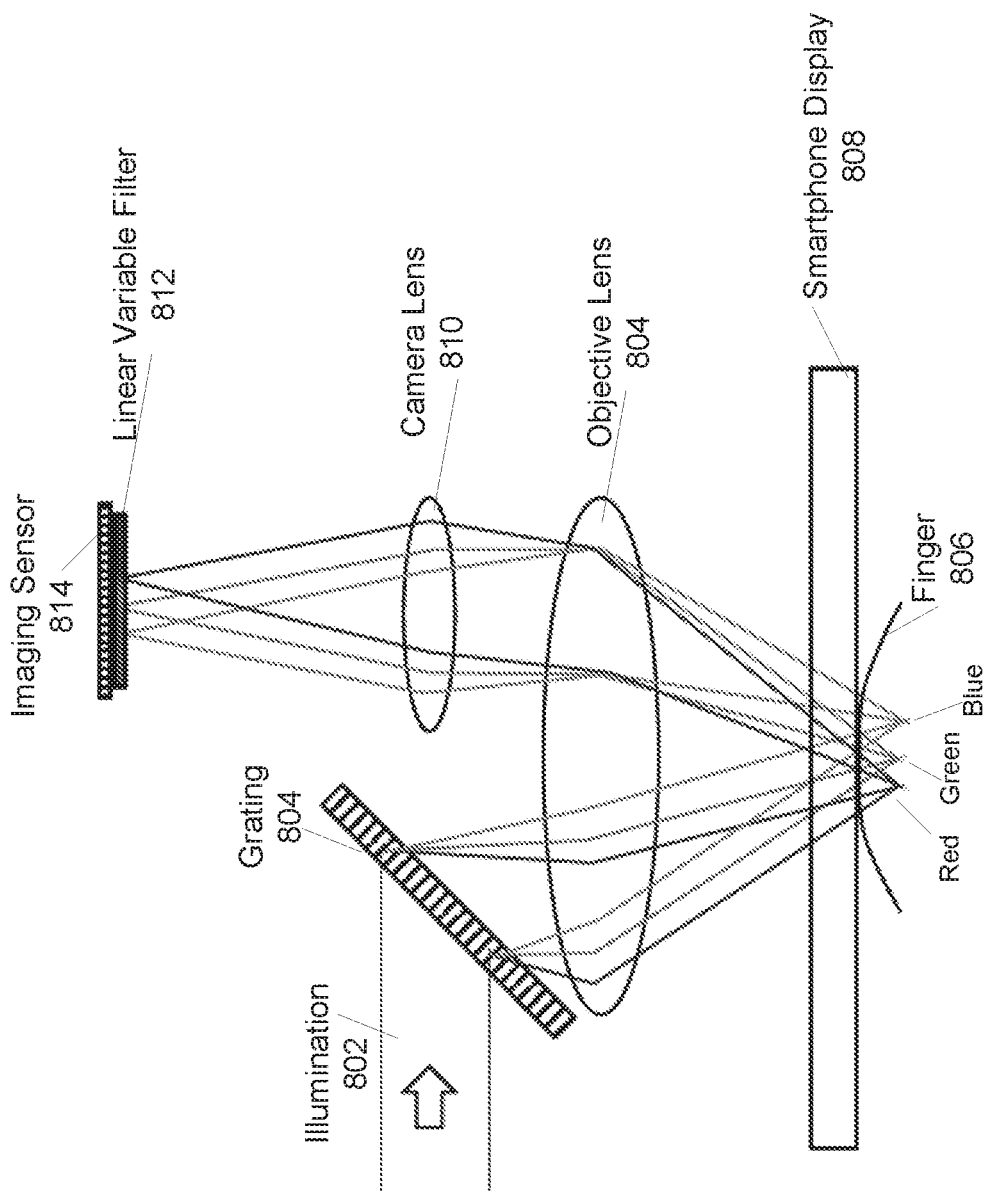
FIG. 8 illustrates an implementation of confocal microscope in a mobile device for fingerprint detection in accordance with an exemplary embodiment.

In some embodiments, the disclosed apertureless confocal microscopes can be implemented as a module inside a smartphone to reliably image fingerprints through the smartphone display. The use of the disclosed confocal microscope for fingerprint detection can be beneficial for replacing and/or augmenting the existing fingerprint detection systems that rely on traditional imaging systems. In such traditional systems, images of the captured fingerprints are often blurry due to, for example, dirt or smudges on the smartphone screen, and produce unreliable detection results. One exemplary embodiment of the disclosed technology for fingerprint detection is illustrated in FIG. 8. The layout of the components in FIG. 8 is similar to FIG. 3 that includes a grating 804 to provide the received illumination 802 to the target (in this case the finger 806 surface), an objective lens 804, a camera lens 810, a linear variable filter 812 and an imaging sensor 814. In the configuration of FIG. 8 an image of a fingerprint from the finger 806 that is placed on the smartphone display 808 (or on the on/off key) is captured at the imaging sensor 814. To allow the capture of a sufficient number of points from the fingerprint, the configuration of FIG. 8 can be designed to capture a larger FOV (e.g., at a cost of providing a lower image resolution) compared to a similar configuration that is used, for example, to analyze skin abnormalities.

Figure 9:
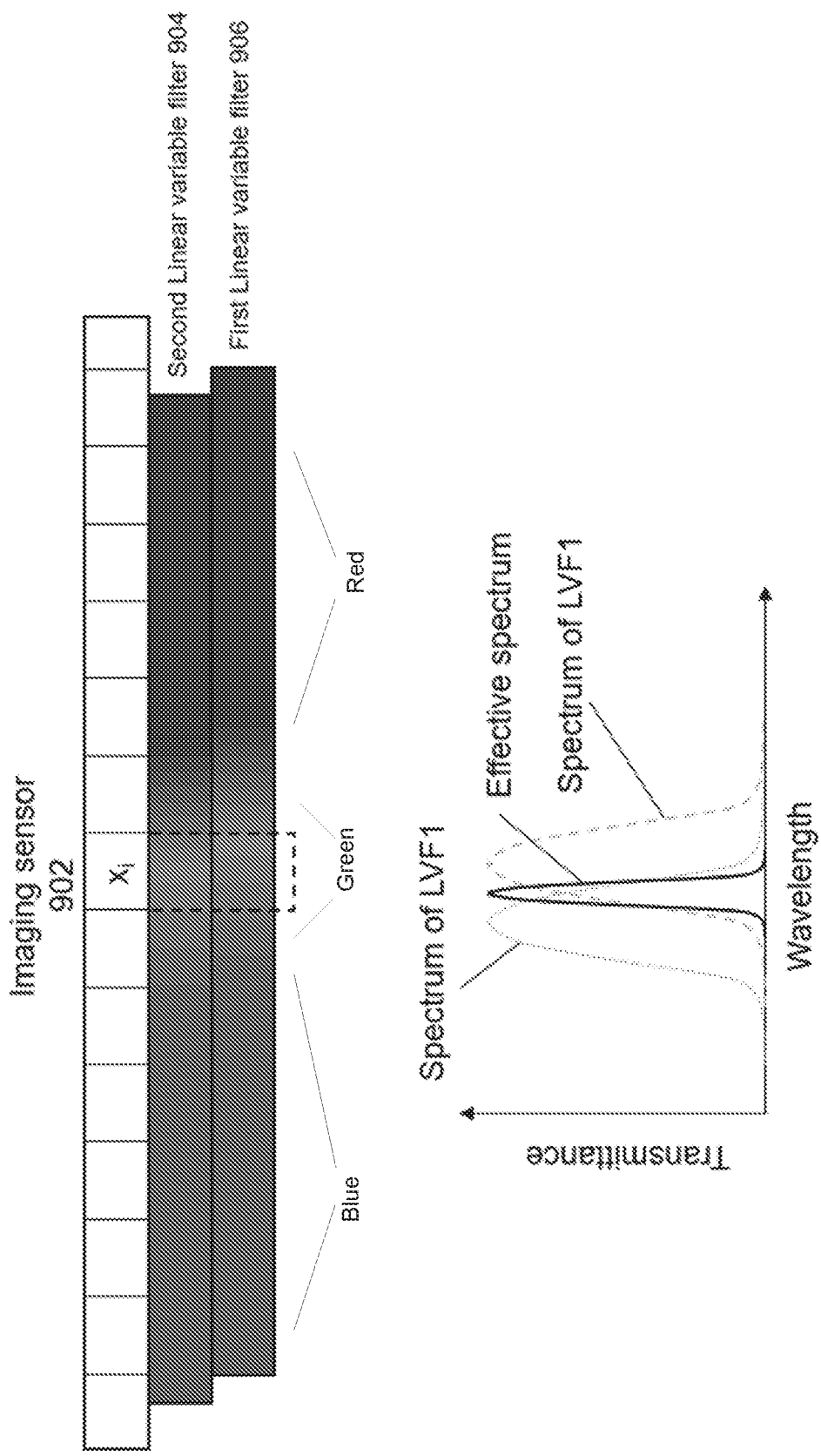
FIG. 9 illustrates an implementation of a linear variable filter in accordance with an exemplary embodiment.

FIG. 9 illustrates an implementation of a linear variable filter in accordance with an exemplary embodiment. Such an implementation can be beneficial where the pass bandwidth (i.e., spectral pass band) of a single linear variable filter is not sufficiently small. The bandwidth of the linear variable filter affects the optical resolution of the confocal microscope: the larger the bandwidth, the poorer the resolution. Thus, in some applications, a smaller bandwidth of the linear variable filter may be required to produce the desired image quality. The configuration in FIG. 9 illustrates one example of a narrow passband variable linear filter that includes a first linear variable filter 906 that is positioned below a second linear variable filter 904 at a small spatial shift relative to one another. An imaging sensor 902 (having a plurality of pixels-a representative pixel, xi, is shown) is positioned to receive the light after passing through both linear variable filters. FIG. 9 illustrates an example embodiment with two identical linear variable filters 904, 906. In some embodiments, the two filters may not be identical as long as the area of spectral overlap of the two filters produces a narrower passband. The illustrative plot of transmission versus wavelength in FIG. 9) shows the smaller passband of the combined filter (effective linear filter transmission spectra) that is formed in region where the transmittances of the two filters overlap.

Figure 10:
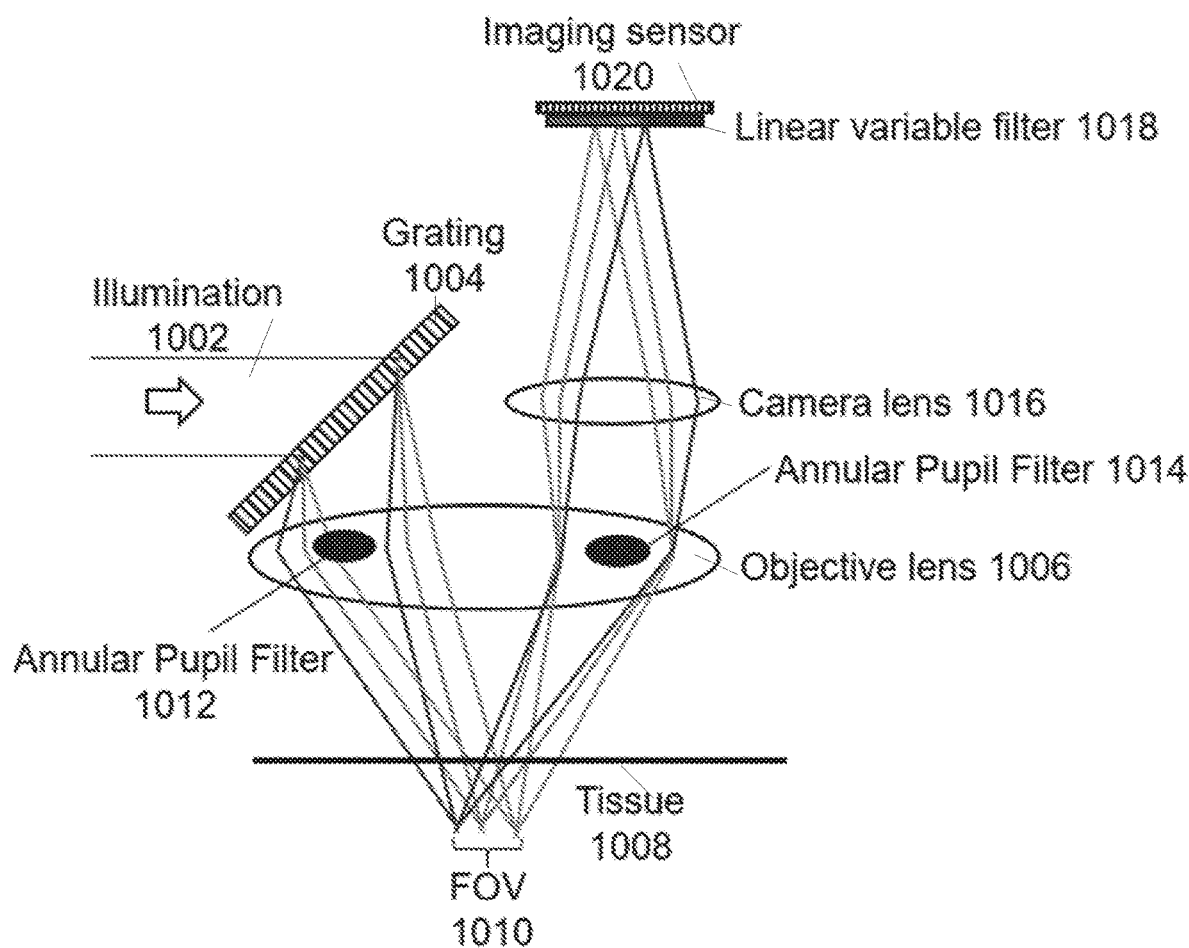
FIG. 10 illustrated another configuration of a confocal microscope including pupil filters in accordance with an exemplary embodiment.

FIG. 10 illustrated another configuration of a confocal microscope in accordance with an exemplary embodiment. The configuration of FIG. 10 is similar to FIG. 3 and includes a grating 1004 that provides the received illumination 1002 to the tissue 1008 via the objective lens 1006: the light reflected from the tissue 1008 is provided to the linear variable filter 1018 by the camera lens 1016, and is sensed by the imaging sensor 1020; the field of view 1010 is also illustrated. In the configuration of FIG. 10, however, annular pupil filters 1012, 1014 are positioned on the pupil plane that can be used in the illumination and/or detection beam paths. The filters can be in the form of annular disks having a beam obstruction in the center thereof. The use of an annular pupil filter increases the depth of the field, which can mitigate alignment errors between the illumination and detection focal points. The increased depth of field can also mitigate a potential resolution degradation due to larger than ideal bandwidth of the linear variable filter.

Figure 11:
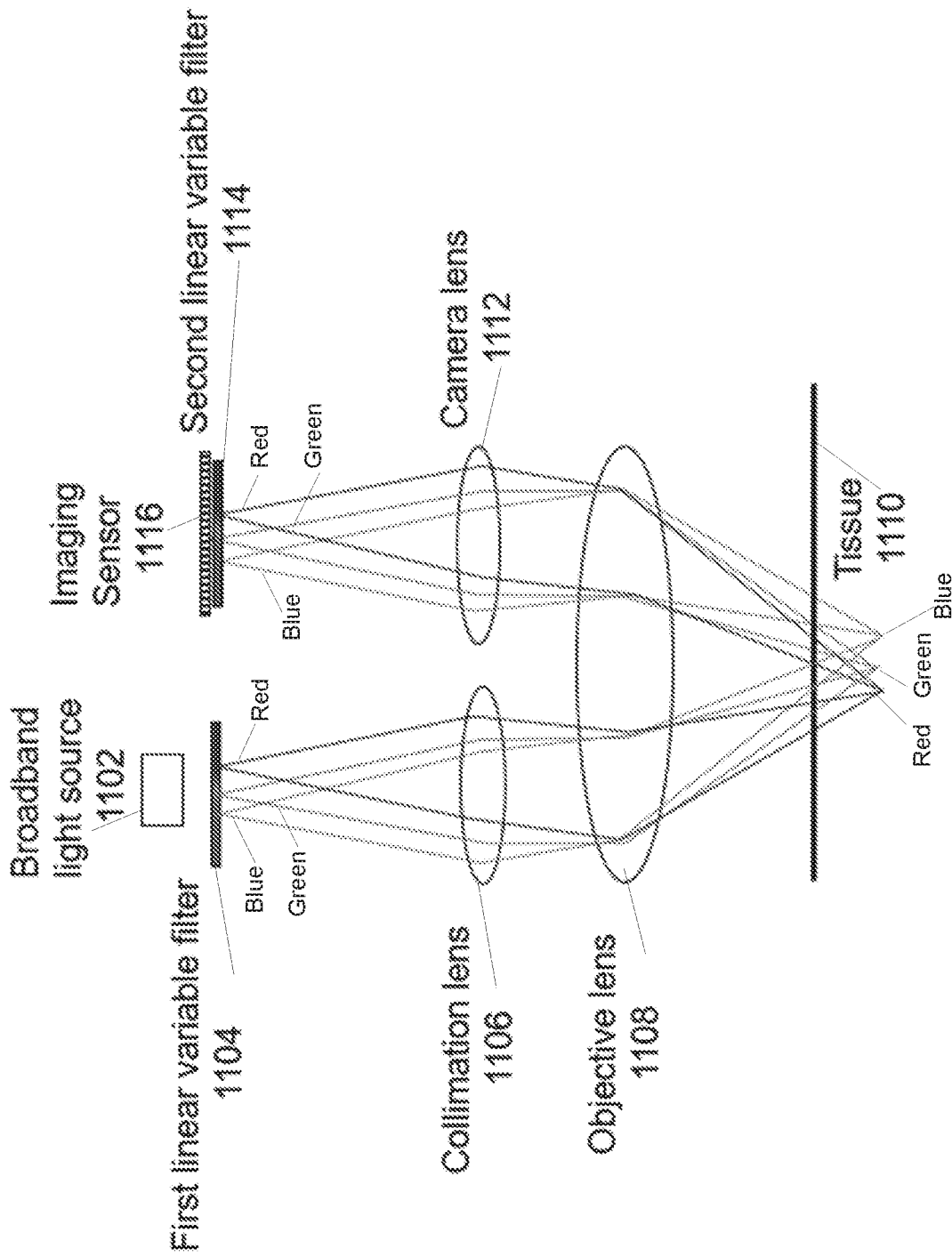
FIG. 11 illustrates an apertureless confocal microscope including two linear variable filters in accordance with an exemplary embodiment.

FIG. 11 illustrates an apertureless confocal microscope in accordance with an exemplary embodiment. In FIG. 11, the illumination is provided by a broadband light source 1102 that is incident on a first linear variable filter 1104 without using any slit aperture. A broadband light source 1104 such as an LED can be used as the light source. Light from the broadband source 1102 is filtered in such a way that each line on the first linear variable filter 1104 allows for the transmission of a narrow bandwidth of the light with a distinctive central wavelength. As a result, light output from the first linear variable filter 1104 can be considered as a set of multiple line sources with distinctive central wavelengths. Light after the first linear variable filter 1104 is collimated by the collimation lens 1106 and focused by the objective lens 1108 onto the tissue 1110. Light reflected back from the tissue 1110 is captured by the objective lens 1108 and focused by the camera lens 1112. Before the light is detected by the imaging sensor 1116, it is filtered by the second linear variable filter 1114 so that each line on the imaging sensor detects a narrow bandwidth with the distinctive central wavelength. By using substantially similar linear variable filters for the first 1104 and the second 1114 linear variable filters, this embodiment eases the design requirement for matching the illumination spectral pattern on the tissue and detection spectral pattern. The illumination optical path is substantially parallel to the optical axis of the objective lens 1108, which facilitates the construction of the confocal microscope as a stylus-like probe and allows for imaging of anatomically hidden body parts such as cervix and nostril.

By the way of example and not limitation, in the some of the disclosed figures, certain optical rays have been identified as red, green and blue to illustrate the path of dispersed rays through the optical systems. It is, however, understood that the disclosed embodiments can operate using different light sources having different spectral characteristics. Similarly, the disclosed linear variable filters can be designed to provide the desired passband characteristics over a particular range of wavelengths.

One aspect of the disclosed embodiments relates to an apertureless confocal microscope that includes a dispersion element positioned to receive a light beam and to produce output beams having different spectral components for illumination of a target. The apertureless confocal microscope further includes one or more lenses positioned to receive reflected beams from the target upon reflection of the output beams from the target, and to focus the reflected beams onto a linear variable filter. The linear variable filter is positioned to receive the focused light from the one or more lenses and to allow a particular range of spectral components of light incident thereon to pass therethrough as a function of a spatial location of the focused light incident on the linear variable filter.

In one example embodiment, the apertureless confocal microscope further includes an image sensor positioned to receive the light after passing through the linear variable filter: such an image sensor includes a plurality of pixels. In another example embodiment, the apertureless confocal microscope further includes a light source to produce the light beam incident on the dispersion element. In one example embodiment, the light source is a line source. According to another example embodiment, the dispersion element is one of a diffraction grating or a prism. In still another example embodiment, the one or more lenses include an objective lens positioned to focus the output beams from the dispersion element on the target, and to collect the reflected beams from the target. In yet another example embodiment, the one or more lenses include a lens to receive the reflected beams after propagation through the objective lens and to focus the reflected beams onto the linear variable filter.

In another example embodiment, the optical axis of the one or more lenses is substantially perpendicular to a surface of the target. In one example embodiment, the apertureless confocal microscope further includes one or more annular pupil filters positioned in one or more of the following locations: on a pupil plane in a path between the dispersion element and the target, or on a pupil plane in a path between the target and the linear variable filter. In another example embodiment, the apertureless confocal microscope is implemented with a mobile communication device to produce an image of a fingerprint, and wherein the target is a finger positioned on a display of the mobile communication device.

Another aspect of the disclosed embodiments relate to an apertureless confocal microscope that includes an optical element positioned to receive a light beam and to produce output beams having different spectral components for illumination of a target. The apertureless confocal microscope further includes one or more lenses positioned to receive reflected beams from the target upon reflection of the output beams from the target, and to focus the reflected beams onto a linear variable filter: the linear variable filter of the apertureless confocal microscope is positioned to receive the focused light from the one or more lenses and to allow a particular range of spectral components of light incident thereon to pass therethrough as a function of a spatial location of the focused light incident on the linear variable filter. In one example embodiment, the optical element is another linear variable filter that is configured to produce the output beams having different spectral components as a set of multiple line sources with distinctive central wavelengths.

Another aspect of the disclosed embodiment relate to an apertureless confocal microscope that includes a high dispersion lens positioned to receive a line output beam and to illuminate a target such that light having different spectral contents are focused onto different depths of the target. The apertureless confocal microscope further includes at least another lens positioned to receive reflected light from the target, and to focus the reflected light onto a linear variable filter. The linear variable filter of this apertureless confocal microscope is positioned to receive the focused light from the at least another lens and to allow a particular range of spectral components of light incident thereon to pass therethrough as a function of a spatial location of the focused light incident on the linear variable filter.

In one example embodiment, the optical axis of the at least another lens is at an oblique angle with respect to a surface of the target. In another example embodiment, the apertureless confocal microscope further includes an image sensor positioned to receive the light that passes through the linear variable filter, where the imaging sensor includes a plurality of pixels. According to another example embodiment, the apertureless confocal microscope also includes magnifier optics positioned to produce an image of the target at a plane that is substantially parallel to a surface of the target. In still another example embodiment, the apertureless confocal microscope includes the light source comprising a slit to produce the line output beam.

In some embodiments, the target is a skin tissue. In still other embodiments, the linear variable filter includes at least a first linear variable filter that is stacked on top of a second linear variable filter with a spatial offset to allow a narrower spectral bandwidth of light to pass through the combination of the first and the second linear variable filters compared to a spectral bandwidth of light that can pass through each of the first or the second linear variable filters. In some example embodiments, the apertureless confocal microscope is implemented within an enclosure having at least a transparent section. For example, the apertureless confocal microscope can be implemented as part of an endoscope. In one example embodiment, the enclosure further includes electronic circuitry to send or receive electronic signals from or to the enclosure to an electronic device that resides outside of the enclosure. In some embodiments, the electronic circuitry is configured to send or receive electronic signals via a wireless transmitter or receiver.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. While operations are depicted in the drawings in a particular order, this should not be understood as requiring that such operations be performed in the particular order shown or in sequential order, or that all illustrated operations be performed, to achieve desirable results. The features of the embodiments described herein may be combined in all possible combinations of methods, apparatus, modules, and systems.

What is claimed is:

1. An apertureless confocal microscope, comprising:
    a dispersion element positioned to receive a light beam and to produce output beams having different spectral components for illumination of a target;
    one or more lenses, a variable linear filter and an imaging sensor, wherein the one or more lenses are positioned to receive reflected beams from the target upon reflection of the output beams from the target, and to focus the reflected beams onto the linear variable filter positioned at the focal plane of the one or more lenses, wherein
    the linear variable filter is positioned to receive the focused reflected beams from the one or more lenses and to allow a particular range of spectral components of the focused reflected beams incident thereon to pass therethrough as a function of a spatial location of the focused reflected beams incident on the linear variable filter, wherein the imaging sensor includes a plurality of pixels, wherein the imaging sensor is positioned immediately adjacent to the linear variable filter at the focal plane to receive the spectral components of the reflected beams after passing through the linear variable filter, wherein the imaging sensor is positioned to allow pixels of the imaging sensor at different spatial locations to capture different spectral components passing through the variable linear filter.

2. The apertureless confocal microscope of claim 1, wherein the dispersion element is one of a diffraction grating or a prism.

3. The apertureless confocal microscope of claim 1, wherein the optical axis of the one or more lenses is substantially perpendicular to a surface of the target.

4. The apertureless confocal microscope of claim 1, further including one or more annular pupil filters positioned in one or more of the following locations:
    on a pupil plane in a path between the dispersion element and the target; or
    on a pupil plane in a path between the target and the linear variable filter.

5. The apertureless confocal microscope of claim 1, wherein the apertureless confocal microscope is implemented with a mobile communication device to produce an image of a fingerprint, and wherein the target is a finger positioned on a display of the mobile communication device.

6. The apertureless confocal microscope of claim 1, further comprising a light source to produce the light beam incident on the dispersion element.

7. The apertureless confocal microscope of claim 6, wherein the light source is a line source.

8. The apertureless confocal microscope of claim 1, wherein the one or more lenses include an objective lens positioned to focus the output beams from the dispersion element on the target, and to collect the reflected beams from the target.

9. The apertureless confocal microscope of claim 8, wherein the one or more lenses include a lens to receive the reflected beams after propagation through the objective lens and to focus the reflected beams onto the linear variable filter.

10. An apertureless confocal microscope, comprising:
    an optical element positioned to receive a light beam and to produce output beams having different spectral components for illumination of a target; and
    one or more lenses, a variable linear filter and an imaging sensor, wherein the one or more lenses are positioned to receive reflected beams from the target upon reflection of the output beams from the target, and to focus the reflected beams onto the linear variable filter positioned at the focal plane of the one or more lenses, wherein
    the linear variable filter is positioned to receive the focused reflected beams from the one or more lenses and to allow a particular range of spectral components of the focused reflected beams incident thereon to pass therethrough as a function of a spatial location of the focused reflected beams incident on the linear variable filter, wherein the imaging sensor includes a plurality of pixels, wherein the imaging sensor is positioned immediately adjacent to the linear variable filter at the focal plane to receive the spectral components of the reflected beams after passing through the linear variable filter, wherein the imaging sensor is positioned to allow pixels of the imaging sensor at different spatial locations to capture different spectral components passing through the variable linear filter.

11. The apertureless confocal microscope of claim 10, wherein the optical element is another linear variable filter that is configured to produce the output beams having different spectral components as a set of multiple line sources with distinctive central wavelengths.

12. An apertureless confocal microscope, comprising:
a high dispersion lens positioned to receive a line output beam from a light source and to illuminate a target such that light having different spectral contents are focused onto different depths of the target; and
at least another lens, a variable linear filter and an imaging sensor, wherein the at least another lens positioned to receive reflected light from the target, and to focus the reflected light onto a linear variable filter positioned at the focal plane of the one or more lenses, wherein
the linear variable filter is positioned to receive the focused reflected light from the at least another lens and to allow a particular range of spectral components of the reflected light incident thereon to pass therethrough as a function of a spatial location of the focused reflected light incident on the linear variable filter, wherein the imaging sensor includes a plurality of pixels, wherein the imaging sensor is positioned immediately adjacent to the linear variable filter at the focal plane to receive the spectral components of the reflected light after passing through the linear variable filter, wherein the imaging sensor is positioned to allow pixels of the imaging sensor at different spatial locations to capture different spectral components passing through the variable linear filter.

13. The apertureless confocal microscope of claim 12, wherein an optical axis of the at least another lens is at an oblique angle with respect to a surface of the target.

14. The apertureless confocal microscope of claim 12, further including magnifier optics positioned to produce an image of the target at a plane that is substantially parallel to a surface of the target.

15. The apertureless confocal microscope of claim 12, further including the light source that includes a slit to produce the line output beam.

16. The apertureless confocal microscope of claim 12, wherein the target is a skin tissue.

17. The apertureless confocal microscope of claim 12, wherein the linear variable filter includes at least a first linear variable filter that is stacked on top of a second linear variable filter with a spatial offset to allow a narrower spectral bandwidth of the reflected light to pass through the combination of the first and the second linear variable filters compared to a spectral bandwidth of the reflected light that can pass through each of the first or the second linear variable filters.

18. The apertureless confocal microscope of claim 12, wherein the apertureless confocal microscope is implemented within an enclosure having at least a transparent section.

19. The apertureless confocal microscope of claim 18, wherein the apertureless confocal microscope is implemented as part of an endoscope.

20. The apertureless confocal microscope of claim 18, wherein the enclosure further includes electronic circuitry to send electrical signals to or receive electronic signals from an electronic device that resides outside of the enclosure.

21. The apertureless confocal microscope of claim 20, wherein the electronic circuitry is configured to send or receive the electronic signals via a wireless transmitter or receiver.

* * * * *